(12) United States Patent
Herdocia

(10) Patent No.: US 9,044,294 B1
(45) Date of Patent: Jun. 2, 2015

(54) DENTAL SUCTION ADAPTER

(71) Applicant: Filiberto Herdocia, Miami, FL (US)

(72) Inventor: Filiberto Herdocia, Miami, FL (US)

(*) Notice: Subject to any disclaimer, the term of this patent is extended or adjusted under 35 U.S.C. 154(b) by 30 days.

(21) Appl. No.: 14/011,019

(22) Filed: Aug. 27, 2013

Related U.S. Application Data

(60) Provisional application No. 61/794,243, filed on Mar. 15, 2013.

(51) Int. Cl.
*A61C 17/06* (2006.01)

(52) U.S. Cl.
CPC .................... *A61C 17/043* (2013.01)

(58) Field of Classification Search
CPC ............... A61C 1/00; A61C 17/043
USPC ...................................... 433/91–96
See application file for complete search history.

(56) References Cited

U.S. PATENT DOCUMENTS

| | | | | |
|---|---|---|---|---|
| 2,005,625 A * | 6/1935 | La Riche | .................. | 433/91 |
| 2,519,595 A * | 8/1950 | Older | .................. | 433/96 |
| RE24,693 E | 9/1959 | Thompson | | |
| 3,256,885 A * | 6/1966 | Higgins et al. | .................. | 604/268 |
| 3,344,523 A * | 10/1967 | Halsey | .................. | 433/96 |
| 3,453,735 A * | 7/1969 | Burt | .................. | 433/96 |
| 3,460,255 A * | 8/1969 | Hutson | .................. | 433/91 |
| 3,713,443 A * | 1/1973 | Fertik | .................. | 604/119 |
| 3,742,607 A * | 7/1973 | Johnson | .................. | 433/91 |
| 3,807,401 A * | 4/1974 | Riggle et al. | .................. | 604/269 |
| 4,049,000 A * | 9/1977 | Williams | .................. | 604/119 |
| 4,083,115 A * | 4/1978 | McKelvey | .................. | 433/96 |
| 4,204,328 A * | 5/1980 | Kutner | .................. | 433/29 |
| 4,265,621 A * | 5/1981 | McVey | .................. | 433/91 |
| 4,281,986 A * | 8/1981 | Erickson | .................. | 433/93 |
| 4,417,874 A * | 11/1983 | Andersson et al. | .................. | 433/96 |
| 4,586,900 A * | 5/1986 | Hymanson et al. | .................. | 433/96 |
| 4,776,793 A * | 10/1988 | La Rocca | .................. | 433/96 |
| 4,865,545 A * | 9/1989 | La Rocca | .................. | 433/96 |
| 4,878,900 A * | 11/1989 | Sundt | .................. | 604/119 |
| 4,883,426 A * | 11/1989 | Ferrer | .................. | 433/91 |
| 5,195,952 A * | 3/1993 | Solnit et al. | .................. | 604/19 |
| 5,295,830 A * | 3/1994 | Shen et al. | .................. | 433/116 |
| 5,441,410 A * | 8/1995 | Segerdal | .................. | 433/93 |
| 5,688,121 A * | 11/1997 | Davis | .................. | 433/96 |
| 5,741,134 A | 4/1998 | Davis | | |
| 5,743,736 A * | 4/1998 | Folko et al. | .................. | 433/96 |
| 5,803,731 A * | 9/1998 | Nordstrom | .................. | 433/96 |
| 5,868,701 A * | 2/1999 | Powers, Jr. | .................. | 604/500 |
| 5,876,384 A * | 3/1999 | Dragan et al. | .................. | 604/264 |
| 5,882,197 A | 3/1999 | Davis et al. | | |
| 6,299,444 B1 * | 10/2001 | Cohen | .................. | 433/91 |
| 7,261,560 B2 | 8/2007 | Abo | | |
| 7,625,207 B2 | 12/2009 | Hershey et al. | | |
| 7,744,371 B1 * | 6/2010 | Griffin et al. | .................. | 433/91 |
| 2013/0164706 A1 * | 6/2013 | Odabashian et al. | .......... | 433/92 |

* cited by examiner

*Primary Examiner* — Cris L Rodriguez
*Assistant Examiner* — Hao D Mai
(74) *Attorney, Agent, or Firm* — Robert C. Montgomery; Montgomery Patent & Design, LLC

(57) ABSTRACT

A dental suction adapter can include a first tube including a tapered portion and a presenting end, the presenting end being configured to fluidly engage an interior of a mouth, and a second tube including a transition tube connected to the tapered portion of the first tube and a connection taper extending from the transition tube opposite the first tube, the connection taper being configured to be connected to an end of an aspirator tube, wherein the adapter is configured to increase a velocity of air at the presenting end compared to a velocity of the fluid at the aspirator tube.

12 Claims, 3 Drawing Sheets

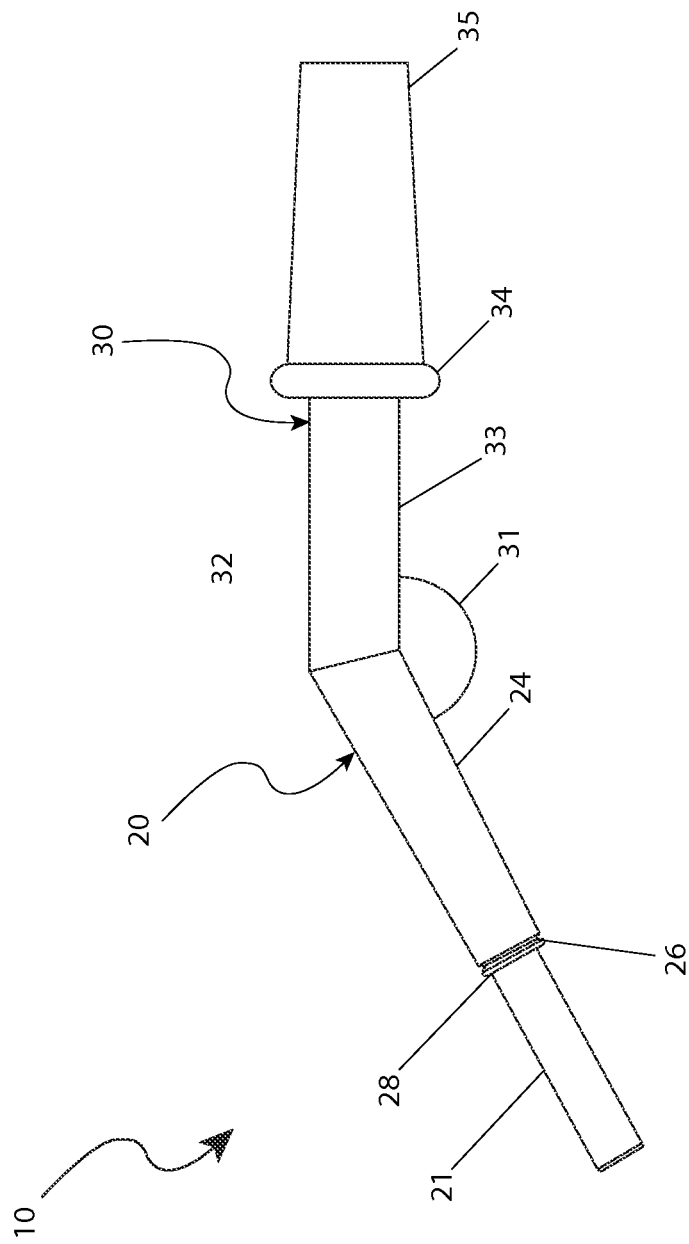

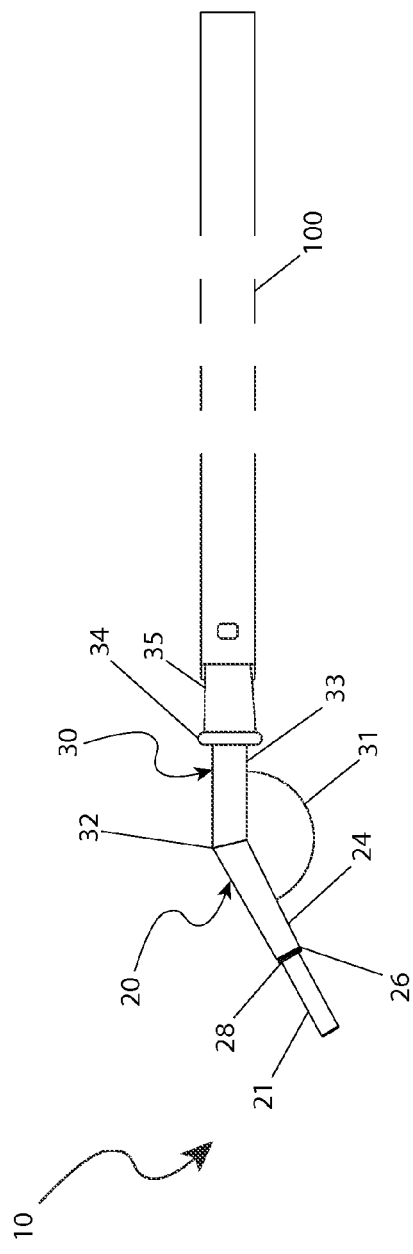
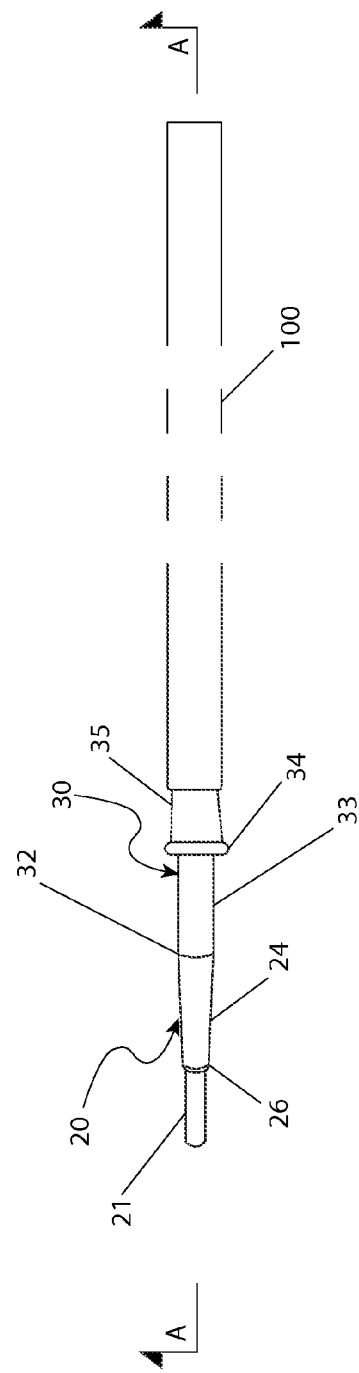

DENTAL SUCTION ADAPTER

RELATED APPLICATIONS

The present invention was first described in and claims the benefit of U.S. Provisional Application No. 61/794,243, filed Mar. 15, 2013, the entire disclosures of which are incorporated herein by reference.

FIELD OF THE INVENTION

The present invention relates generally to aspirators, and more particularly, to a breakaway adapter connected to an aspirator tube and configured to increase velocity of an airflow delivery to the aspirator tube.

BACKGROUND OF THE INVENTION

During the process of various dental activities, there is a need for high-speed suction and surgical suction aids. Typical dental surgical suction devices use two (2) hoses to provide such capabilities. Of course such devices are more costly than those that utilize only one (1) suction hose. However, those who use only single hose devices are burdened with having to change the hose connections between high-speed suction and surgical suction connectors. This process translates directly into lost time, reduced productivity, and increased costs.

Accordingly, there exists a need for a means by which a single hose dental suction device can be quickly changed from a high-speed suction connection to a surgical suction connection, without the disadvantages as described above.

SUMMARY OF THE INVENTION

The inventor has recognized the aforementioned inherent problems and lack in the art and observed that there is a need for a device configured to be utilized with a dental suction device to effectively adjust (e.g., increase) the velocity of an airflow delivery to the aspirator tube. The development of the present invention, which will be described in greater detail herein, substantially departs from conventional solutions to provide a dental suction adapter and in doing so fulfills this need.

In one (1) embodiment, the disclosed dental suction adapter can include a first tube being configured to fluidly engage an area, and a second tube connected to the first tube, the second tube being configured to connect to a pneumatic tube, wherein the adapter is configured to increase a velocity of a fluid at the first tube compared to a velocity of the fluid at the pneumatic tube.

In another embodiment, the disclosed dental suction adapter can include a first tube including a tapered portion and a presenting end, the presenting end being configured to fluidly engage an interior of a mouth, and a second tube including a transition tube connected to the tapered portion of the first tube and a connection taper extending from the transition tube opposite the first tube, the connection taper being configured to be connected to an end of an aspirator tube, wherein the adapter is configured to increase a velocity of air at the presenting end compared to a velocity of the fluid at the aspirator tube.

Furthermore, the described features and advantages of the disclosed dental suction adapter can be combined in various manners and embodiments as one skilled in the relevant art will recognize after reading the present disclosure. The disclosure can be practiced without one (1) or more of the features and advantages described in any particular embodiment.

Further advantages of the present disclosure will become apparent from a consideration of the drawings and ensuing description.

BRIEF DESCRIPTION OF THE DRAWINGS

The advantages and features of the present disclosure will become better understood with reference to the following more detailed description and claims taken in conjunction with the accompanying drawings, in which like elements are identified with like symbols, and in which:

FIG. 1 is an elevation view of a dental suction adapter 10 in accordance to the preferred embodiment of the present invention;

FIG. 2a is an elevation view of the dental suction adapter 10 inserted into an aspirator tube 100 in accordance to the preferred embodiment of the present invention;

FIG. 2b is a top view of the dental suction adapter 10 inserted into an aspirator tube 100 in accordance to the preferred embodiment of the present invention; and, FIG. 3 is a section view along line A-A as seen in FIG. 2b of the dental suction adapter 10 in accordance to the preferred embodiment of the present invention.

Figure 3:
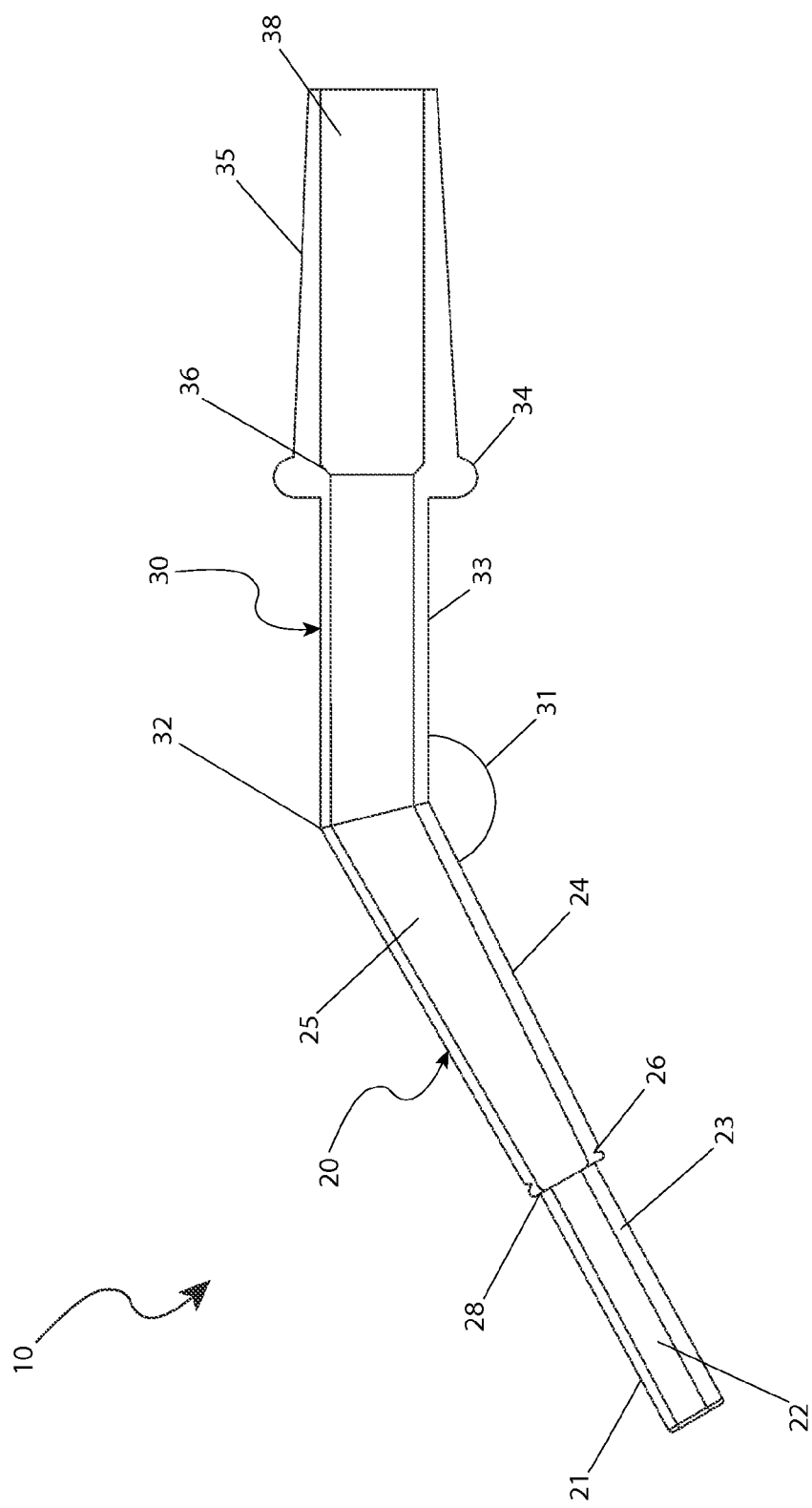

DESCRIPTIVE KEY 10 dental suction adapter
20 first tube
21 presenting end
22 straight bore channel
23 tube wall
24 first taper
25 tapered bore channel
26 snapping point
28 nexus
30 second tube
31 disposition angle
32 tube interface
33 transition tube
34 collar
35 connection taper
36 bore termination
38 final bore
100 aspirator tube

DETAILED DESCRIPTION OF THE PREFERRED EMBODIMENT

In accordance with the invention, the best mode is presented in terms of the described embodiments, herein depicted within FIGS. 1 through 3. However, the disclosure is not limited to the described embodiments and a person skilled in the art will appreciate that many other embodiments are possible without deviating from the basic concept of the disclosure and that any such work around will also fall under its scope. It is envisioned that other styles and configurations can be easily incorporated into the teachings of the present disclosure, and only certain configurations have been shown and described for purposes of clarity and disclosure and not by way of limitation of scope.

It can be appreciated that, although such terms as first, second, etc. may be used herein to describe various elements, these elements should not be limited by these terms. These terms are only used to distinguish one (1) element from another element. Thus, a first element discussed below could be termed a second element without departing from the scope of the present invention. In addition, as used herein, the singular forms "a", "an" and "the" are intended to include the plural forms as well, unless the context clearly indicates otherwise. It also will be understood that, as used herein, the term "comprising" or "comprises" is open-ended, and includes one (1) or more stated elements, steps or functions without precluding one (1) or more unstated elements, steps or functions. Relative terms such as "front" or "rear" or "left" or "right" or "top" or "bottom" or "below" or "above" or "upper" or "lower" or "horizontal" or "vertical" may be used herein to describe a relationship of one (1) element, feature or region to another element, feature or region as illustrated in the figures. It should be understood that these terms are intended to encompass different orientations of the device in addition to the orientation depicted in the figures. It should also be understood that when an element is referred to as being "connected" to another element, it can be directly connected to the other element or intervening elements may be present. In contrast, when an element is referred to as being "directly connected" to another element, there are no intervening elements present. It should also be understood that the sizes and relative orientations of the illustrated elements are not shown to scale, and in some instances they have been exaggerated for purposes of explanation.

Referring to FIGS. 1-3, disclosing a dental suction adapter (herein referred to as the "device") 10, where like reference numerals represent similar or like parts. The device 10 is configured to quickly increase the velocity of air entering an aspirator tube 100 without changing to another aspirator tube 100 with a smaller diameter.

Those skilled in the art will appreciate that the velocity of a fluid, at any given flow rate, through any channel is inversely proportional to the cross-sectional area of that channel. The force that moving air is able to exert on any object (e.g., a collection of fluids in a patient's oral cavity) is directly proportional to the square of the velocity of the air. Therefore, increasing the velocity of the air entering the aspirator tube 100 has a significant effect on the size of the particle that can be carried in the airflow or the ease with which a particle can be carried.

Referring now to FIG. 1, the device 10 can include a first tube 20 and a second tube 30. The first tube 20 can be disposed at a non-zero angle relative to the second tube 30. For example, the non-zero angle 31 can be between approximately one hundred forty degrees (140°) and one hundred sixty-five degrees (165°). As another example, the disposition angle 31 can be approximately one hundred fifty-two degrees (152°) for an optimum balance of comfort and fit.

The device 10 can be approximately ninety-seven millimeters (97 mm) (3.82 in) in length. An example material of construction for the device 10 can be a rigid or semi-rigid medical grade plastic that is suitable for use in an autoclave. However, those skilled in the art will appreciate that other materials can be utilized without limitation. The device 10 can be made of an opaque material due to the nature of fluids and material being transferred within the device 10. However, alternate embodiments can utilize a translucent or a transparent material of construction.

The first tube 20 can include a first portion and a second portion. The second portion can form a presenting end 21 opposite the second tube 30. The presenting end 21 can include a continuous tubular wall 23 defining a straight bore channel 22 (FIG. 3). The presenting end 21 can be approximately twenty millimeters (20 mm) (0.79 in) in length The tube wall 23 can include a uniform thickness.

The first portion of the first tube 20 can extend from the second tube 30. The first portion of the first tube 20 can terminate at a concentric first taper 24 proximate the presenting end 21. The first taper 24 can be approximately thirty millimeters (30 mm) (1.18 in) long and can define a tapered bore channel 25. The bore channel 25 can include an immediately larger inside diameter than the presenting end 21 (FIG. 3).

Disposed just beyond a nexus 28 of the presenting end 21 and the first taper 24 is a snapping point 26. This snapping point 26 can include a radical, local reduction of the thickness of the tube wall 23, such that the structural integrity of the tube wall 23 can be compromised and the presenting end 21 can be separated from the first taper 24 with relative ease. In an example implementation, the need for breaking off the presenting end 21 of the first tube 20 can arise if a user (e.g., a dentist) determined that the velocity of air in the presenting end 21 was too great for the circumstances of the current procedure (e.g., a dental procedure).

Referring to FIG. 3, the first tube 20 and the second tube 30 can be fused together at a tube interface 32 (e.g., at a meeting location of the first tube 20 and the second tube 30). The second tube 30 can be a single unitary member. The second tube 30 can be approximately fifty-three millimeters (53 mm) (2.09 in) long. The second tube 30 can include various regions (e.g., rather than individual sections or pieces). For example, the second tube 30 can include a transition tube 33, a collar 34, and a connection taper 35.

The transition tube 33 can include a uniform diameter and a uniform wall thickness. The second tube 30 can terminate at the connecting taper 35. The connecting taper 35 can include a uniform internal diameter defining a final bore 38 configured to maintain the air velocity. The bore termination 36 can be configured or fashioned to avoid the development of eddy currents.

Referring to FIGS. 2a and 2b, the exterior wall of the connecting taper 35 can be tapered to provide an original diameter that is configured to be inserted inside of an aspirator tube 100. For example, the connecting taper 35 can include an increasing successive diameter to ultimately provide an interference fit within an end of the aspirator tube 100. The collar 34 can be configured to provide a handling (e.g., gripping) mechanism on the second tube 30 to exert sufficient force to insert the device 10 into the aspirator tube 100.

It is envisioned that other styles and configurations of the disclosed device 10 can be easily incorporated into the teachings of the present disclosure, and only certain particular configurations have been shown and described for purposes of clarity and disclosure and not by way of limitation of scope.

In an example implementation, a user can utilize the example embodiments of the device 10 in a simple and straightforward manner with little or no training. For example, in an example implementation, the device 10 can be used with high-speed suction devices, such as those used in dental procedures.

As indicated in FIGS. 2a and 2b, upon initial purchase or acquisition of the device 10, it can be installed to an aspirator tube 100. For example, the connection taper 35 of the second tube 30 can be received by an open end of the aspirator tube 100. The device 10 can be used to clear fluids, or other materials, from an area involved in a dental procedure to assist the user in the successful accomplishment of that procedure.

The foregoing embodiments of the disclosed dental suction adapter have been presented for purposes of illustration and description. They are not intended to be exhaustive or to limit the invention and method of use to the precise forms disclosed. It can be appreciated by one skilled in the art that other styles, configurations, and modifications of the invention can be incorporated into the teachings of the present disclosure upon reading the specification and that the embodiments shown and described are for the purposes of clarity and disclosure and to limit the scope. The embodiments have been chosen and described in order to best explain the principles and practical application in accordance with the invention to enable those skilled in the art to best utilize the various embodiments with expected modifications as are suited to the particular use contemplated. The present application includes such modifications and is limited only by the scope of the claims.

What is claimed is:

1. A suction adapter device comprising:
a unitary tubular member comprising a first tube portion comprising a first end and an opposed second end configured to fluidly communicate with an area and a second tube portion comprising a first end and an opposed second end, said first tube portion and said second tube portion forming a continuous tubular wall defining a fluid channel between said first end of said second tube portion and said second end of said first tube portion, said first tube portion being disposed at an obtuse angle relative to said second tube portion,
wherein said second tube portion comprises:
a connection portion comprising a connection first end and an opposed connection second end, said connection portion further comprising a constant cross-sectional internal diameter from said connection first end to said connection second end, said connection portion further comprising an increasing cross-sectional external diameter from said connection first end to said connection second end configured to be received by said pneumatic suction device;
a transition portion comprising a transition first end extending from said connection second end and an opposed transition second end, said transition portion further comprising a constant cross-sectional internal diameter from said transition first end to said transition second end;
wherein said first tube portion comprises:
a tapered portion comprising a tapered first end extending from said transition second end and an opposed tapered second end said tapered portion further comprising decreasing cross-sectional internal diameter from said tapered first end to said tapered second end configured to increase a fluid velocity from said tapered first end to said tapered second end;
a presenting portion detachable from said tapered portion, said presenting portion comprising a presenting first end extending from said tapered second end and an opposed presenting second end, said presenting portion further comprising a constant cross-sectional internal diameter from said presenting first end to said presenting second end, said cross-sectional internal diameter of said presenting portion being smaller than said cross-sectional internal diameter of said tapered portion at said tapered second end; and,
a weakening feature disposed at a nexus between said tapered second end and said presenting first end to detach said presenting portion from said tapered portion; and,
wherein detachment of said presenting portion increases a cross-sectional internal diameter of said second end of said first tube portion.

2. The device of claim 1, wherein said weakening feature comprises a circumferential snapping point between said tapered second end and said presenting first end to separate said presenting portion from said tapered portion in response to a tensile force.

3. The device of claim 2, wherein said snapping point comprises a circumferential reduction in a thickness of said tubular wall at said nexus between said tapered portion and said presenting portion.

4. The device of claim 1, wherein said obtuse angle comprises an angle between 140° and 165°.

5. The device of claim 1, wherein said obtuse angle comprises a 152° angle.

6. The device of claim 1, wherein said first tube portion defines a first channel portion of said fluid channel, and wherein said second tube portion defines a second channel portion of said fluid channel.

7. The device of claim 6, wherein second channel portion is shaped to eliminate eddy currents proximate a transition between said connection portion and said transition portion.

8. The device of claim 1, wherein said second tube portion further comprises:
a collar disposed circumferentially around said transition portion proximate said connection second end.

9. The device of claim 1, further comprising said pneumatic suction device.

10. The device of claim 9, wherein said pneumatic suction device comprises a dental evacuation device comprising an aspirator tube, wherein said connection portion is insertably connected within said aspirator tube, and wherein said area comprises a dental patient's mouth.

11. The device of claim 10, wherein said tubular wall of said connection portion is flat from said connection first end to said connection second end and is configured to be smoothly inserted and removed from within said aspirator tube.

12. The device of claim 1, wherein said tubular wall of said connection portion is flat from said connection first end to said connection second end and is configured to be smoothly inserted and removed from within said pneumatic suction device.

\* \* \* \* \*